US010884233B2

(12) United States Patent
Adachi

(10) Patent No.: US 10,884,233 B2
(45) Date of Patent: Jan. 5, 2021

(54) IMAGING APPARATUS AND ENDOSCOPE SYSTEM

(71) Applicant: OLYMPUS CORPORATION, Tokyo (JP)

(72) Inventor: Satoru Adachi, Tsuchiura (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/434,223

(22) Filed: Jun. 7, 2019

(65) Prior Publication Data

US 2019/0285870 A1    Sep. 19, 2019

Related U.S. Application Data

(63) Continuation of application No. PCT/JP2017/036846, filed on Oct. 11, 2017.

(30) Foreign Application Priority Data

Dec. 21, 2016 (JP) ................................. 2016-248370

(51) Int. Cl.
*G02B 23/24* (2006.01)
*A61B 1/045* (2006.01)
(Continued)

(52) U.S. Cl.
CPC ............ *G02B 23/2484* (2013.01); *A61B 1/04* (2013.01); *A61B 1/045* (2013.01); *G02B 23/24* (2013.01); *H04N 5/3698* (2013.01); *H04N 5/378* (2013.01)

(58) Field of Classification Search
None
See application file for complete search history.

(56) References Cited

U.S. PATENT DOCUMENTS 4,429,327 A * 1/1984 Oakley ................ H04N 7/0803
348/389.1
4,672,449 A * 6/1987 Kraus ...................... G09G 1/04
348/511
(Continued)

FOREIGN PATENT DOCUMENTS

JP    2000-165759 A       6/2000
JP    2000165759 A   *   6/2000   ............. H04N 5/335
(Continued)

OTHER PUBLICATIONS

International Search Report dated Dec. 5, 2017 issued in PCT/JP2017/036846.
(Continued)

*Primary Examiner* — Reza Aghevli
(74) *Attorney, Agent, or Firm* — Scully, Scott, Murphy & Presser, P.C.

(57) ABSTRACT

An imaging apparatus includes an image sensor and a phase comparison circuit. The image sensor includes, a pixel configured to generate a video signal, a readout circuit configured to read out the video signal, an output circuit configured to output the video signal to a signal processor, a clock generation circuit configured to generate a first clock, and a first control circuit configured to cause the signal processor to output the video signal in accordance with the first clock and a synchronization signal generated by the signal processor. The phase comparison circuit makes a phase comparison between the video signal and a second clock generated by the signal processor. The clock generation circuit generates the first clock based on a power supply voltage in accordance with the phase difference signal.

6 Claims, 6 Drawing Sheets

(51) Int. Cl.
*H04N 5/369* (2011.01)
*H04N 5/378* (2011.01)
*A61B 1/04* (2006.01)

(56) References Cited

U.S. PATENT DOCUMENTS

| | | | | |
|---|---|---|---|---|
| 5,142,376 | A * | 8/1992 | Ogura | H04N 1/646 |
| | | | | 386/204 |
| 5,406,329 | A * | 4/1995 | Kashimura | H03M 1/12 |
| | | | | 348/175 |
| 5,598,274 | A * | 1/1997 | Ogura | H04N 9/896 |
| | | | | 386/207 |
| 5,990,860 | A * | 11/1999 | Takeuchi | G09G 5/391 |
| | | | | 345/667 |
| 6,097,777 | A * | 8/2000 | Tateishi | H03L 7/087 |
| | | | | 375/376 |
| 6,724,381 | B2 * | 4/2004 | Sakashita | G09G 5/008 |
| | | | | 345/213 |
| 7,671,644 | B2 * | 3/2010 | Yan | H03H 11/265 |
| | | | | 327/149 |
| 7,948,661 | B2 * | 5/2011 | Tsukahara | H04N 1/40056 |
| | | | | 358/445 |
| 8,035,433 | B2 * | 10/2011 | Yan | H03H 11/265 |
| | | | | 327/158 |
| 8,957,720 | B2 * | 2/2015 | Miyanishi | H03L 7/0812 |
| | | | | 327/299 |
| 9,609,258 | B2 * | 3/2017 | Hagihara | H03M 1/12 |
| 2003/0156107 | A1 * | 8/2003 | Sakashita | G09G 5/008 |
| | | | | 345/213 |
| 2007/0273421 | A1 * | 11/2007 | Yan | H03H 11/265 |
| | | | | 327/261 |
| 2008/0106748 | A1 * | 5/2008 | Tsukahara | H04N 1/40056 |
| | | | | 358/1.1 |
| 2009/0213212 | A1 * | 8/2009 | Nakamura | A61B 1/00006 |
| | | | | 348/65 |
| 2010/0123489 | A1 * | 5/2010 | Yan | H03H 11/265 |
| | | | | 327/149 |
| 2014/0002170 | A1 * | 1/2014 | Miyanishi | H03L 7/07 |
| | | | | 327/299 |

FOREIGN PATENT DOCUMENTS

| | | | | |
|---|---|---|---|---|
| JP | 2009-201540 | A | | 9/2009 |
| JP | 2013-132385 | A | | 7/2013 |
| JP | 2013-146001 | A | | 7/2013 |
| JP | 2013146001 | A * | 7/2013 | ............ H04N 5/232 |
| JP | 2014-212452 | A | | 11/2014 |
| JP | 2016-111557 | A | | 6/2016 |

OTHER PUBLICATIONS

English translation of International Preliminary Report on Patentability dated Jul. 4, 2019, together with the Written Opinion received in related International Application No. PCT/JP2017/036846.

* cited by examiner

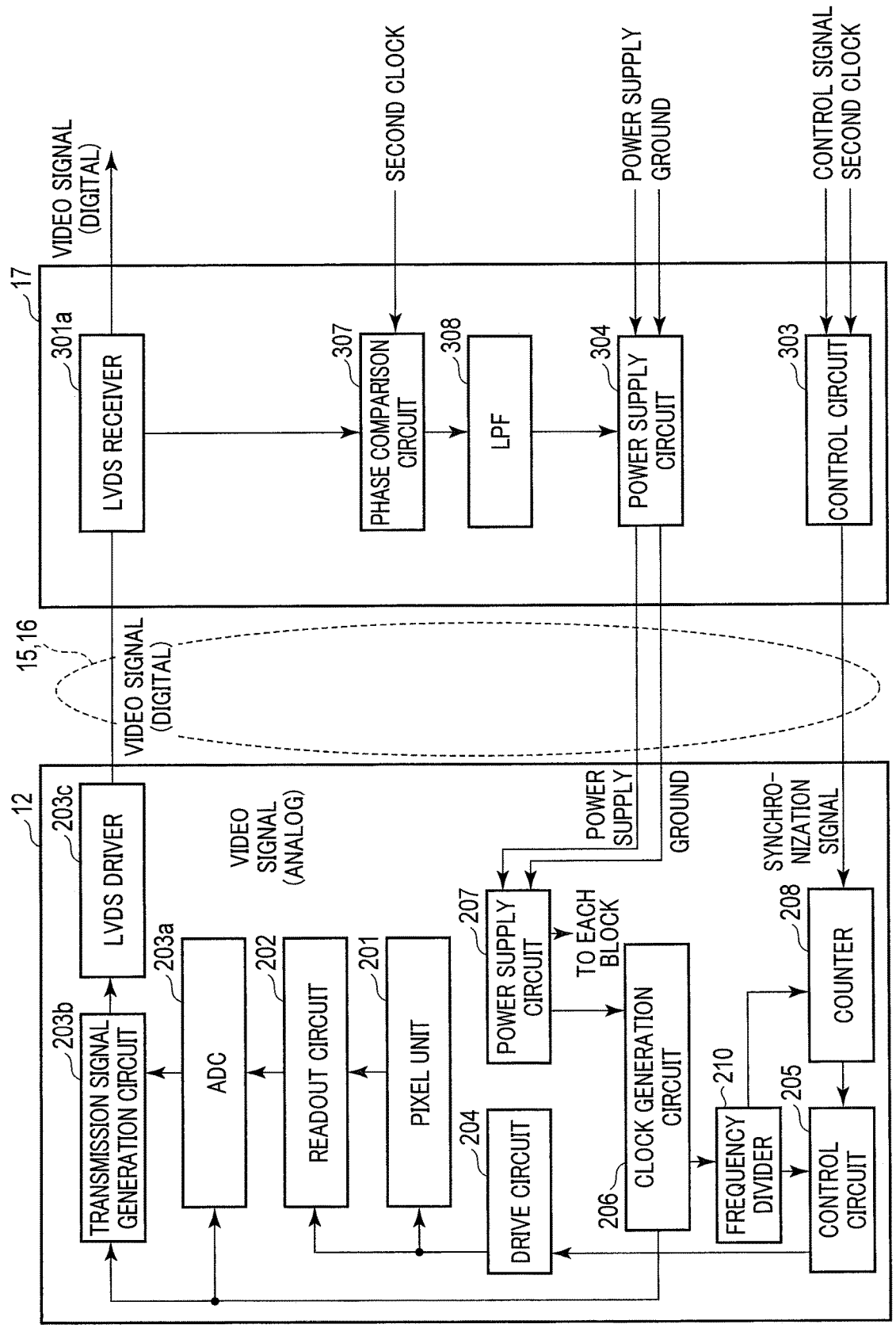
F I G. 3

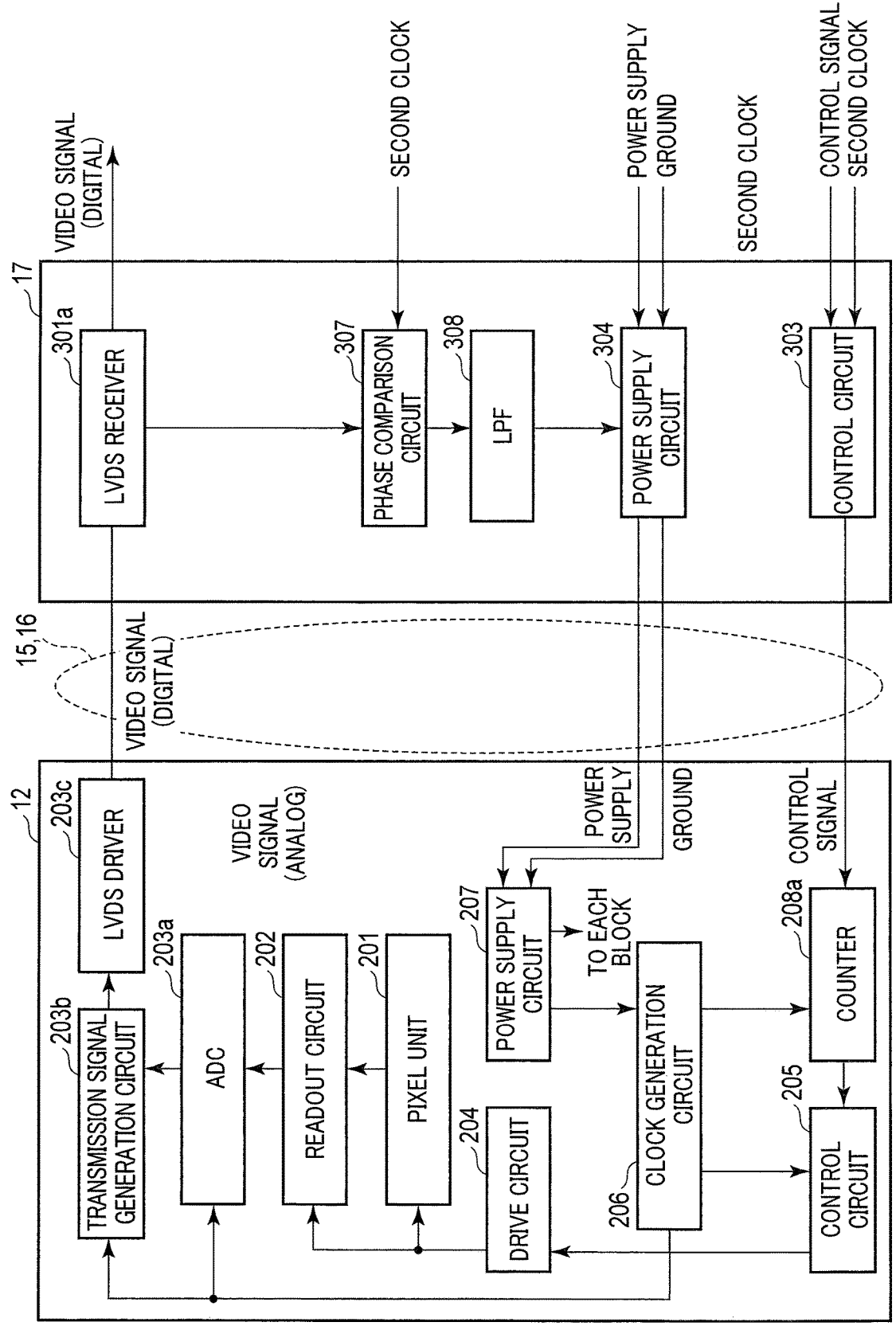
F I G. 4

IMAGING APPARATUS AND ENDOSCOPE SYSTEM

CROSS-REFERENCE TO RELATED APPLICATIONS

This application is a Continuation Application of PCT Application No. PCT/JP2017/036846, filed Oct. 11, 2017 and based upon and claiming the benefit of priority from the prior Japanese Patent Application No. 2016-248370, filed Dec. 21, 2016, the entire contents of both of which are incorporated herein by reference.

FIELD

Exemplary embodiments relate to an imaging apparatus and an endoscope system comprising the same.

BACKGROUND

In recent years, in the field of imaging apparatus such as an endoscope, there has been a demand for decreasing the diameter of the scope. Reducing the number of signal lines connected to an image sensor is a conceivable means of achieving a decreased diameter. For the signal lines connected to the image sensor, at least three signal lines are necessary for a video signal line, a power supply line, and a ground line. In this case, however, there is a need to generate, inside the image sensor, a clock for driving the image sensor, as in the configuration described in Jpn. Pat. Appln. KOKAI Publication No. 2013-132385.

SUMMARY

According to an embodiment, there is provided an imaging apparatus, comprising: an image sensor, including: a pixel configured to generate a video signal; a readout circuit configured to read out the video signal generated by the pixel; an output circuit configured to output the video signal read out by the readout circuit to a signal processor; a clock generation circuit configured to generate a first clock for driving the pixel, the readout circuit, and the output circuit; and a first control circuit configured to cause the signal processor to output the video signal from the output circuit in accordance with the first clock and a synchronization signal generated by the signal processor; and a phase comparison circuit provided outside the image sensor, configured to make a phase comparison between the video signal output from the output circuit and a second clock generated by the signal processor, and output a phase difference signal indicating a phase comparison result, wherein the clock generation circuit generates the first clock based on a power supply voltage in accordance with the phase difference signal.

According to an embodiment, there is provided an imaging apparatus, comprising: an image sensor, including: a pixel configured to generate a video signal; a readout circuit configured to read out the video signal generated by the pixel; an output circuit configured to output the video signal read out by the readout circuit to a signal processor; a clock generation circuit configured to generate a first clock for driving the pixel, the readout circuit, and the output circuit; and a first control circuit configured to cause the signal processor to output the video signal from the output circuit in accordance with the first clock and a reset signal; and a phase comparison circuit provided outside the image sensor, configured to make a phase comparison between the video signal output from the output circuit and a second clock generated by the signal processor, and output a phase difference signal indicating a phase comparison result, wherein the clock generation circuit generates the first clock based on a power supply voltage in accordance with the phase difference signal.

According to an embodiment, there is provided an endoscope system, comprising: an insertion section provided with an image sensor, including: a pixel configured to generate a video signal, a readout circuit configured to read out the video signal generated by the pixel; an output circuit configured to output the video signal read out by the readout circuit to a signal processor; a clock generation circuit configured to generate a first clock for driving the pixel, the readout circuit, and the output circuit; and a first control circuit configured to cause the signal processor to output the video signal from the output circuit in accordance with the first clock and a synchronization signal generated by the signal processor; and a phase comparison circuit provided outside the image sensor, make a phase comparison between the video signal output from the output circuit and a second clock generated by the signal processor, and output a phase difference signal indicating a phase comparison result, wherein the clock generation circuit generates the first clock based on a power supply voltage in accordance with the phase difference signal.

According to an embodiment, there is provided an endoscope system, comprising: an insertion section provided with an image sensor, including: a pixel configured to generate a video signal; a readout circuit configured to read out the video signal generated by the pixel unit; an output circuit configured to output the video signal read out by the readout circuit to a signal processor; a clock generation circuit configured to generate a first clock for driving the pixel, the readout circuit, and the output circuit; and a first control circuit configured to cause the signal processor to output the video signal from the output circuit in accordance with the first clock and a reset signal; and a phase comparison circuit provided outside the image sensor, configured to make a phase comparison between the video signal output from the output circuit and a second clock generated by the signal processor, and output a phase difference signal indicating a phase comparison result, wherein the clock generation circuit generates the first clock based on a power supply voltage in accordance with the phase difference signal.

Advantages of the embodiments will be set forth in the description which follows, and in part will be obvious from the description, or may be learned. The advantages may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments, and together with the general description given above and the detailed description of the embodiments given below, serve to explain the principles.

FIG. 3 is a diagram showing a detailed configuration of an image sensor and a connector according to Modification 1;

FIG. 4 is a diagram showing a detailed configuration of an image sensor and a connector according to 1 and a connector according to Modification 2;

DETAILED DESCRIPTION

Figure 1:
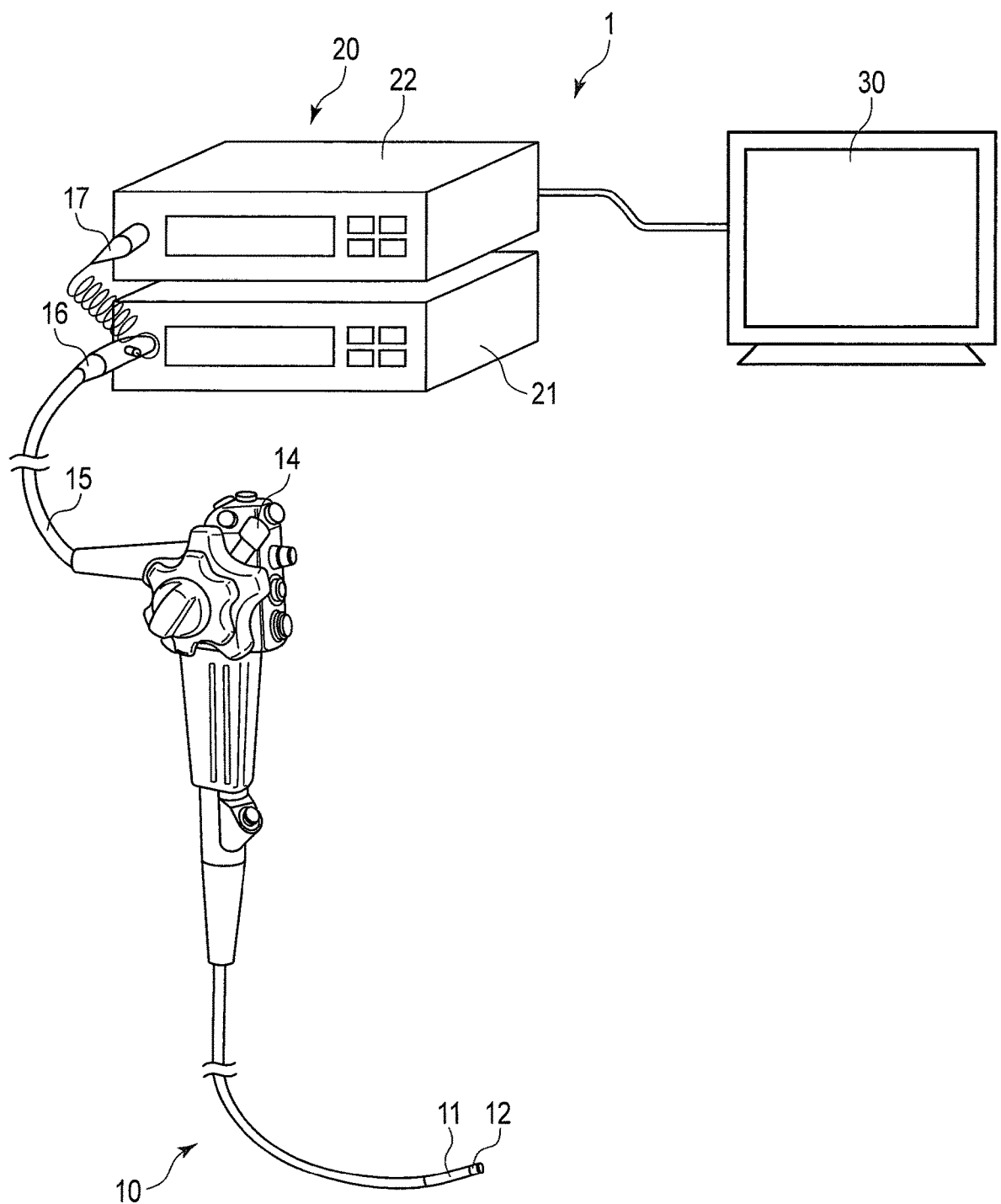
FIG. 1 is a diagram showing a schematic configuration of an endoscope system including an imaging apparatus according to an embodiment.

Embodiments of the present invention will now be described with reference to the accompanying drawings. FIG. 1 is a diagram showing a schematic configuration of an endoscope system including an imaging apparatus according to an embodiment of the present invention. An endoscope system 1 of FIG. 1 includes a scope 10, a controller 20, and a monitor 30. The scope 10 transmits a video signal inside a subject body to an image processor 22 of the controller 20. The image processor 22 processes the video signal transmitted from the scope 10. The monitor 30 displays the video based on the video signal processed by the controller 20.

The scope 10 functioning as the imaging apparatus in the present embodiment includes an insertion section 11, an operation unit 14, a cable 15, a connector 16, and a connector 17.

The insertion section 11 is a section inserted into the subject body. An image sensor 12 is provided inside the distal end of the insertion section 11. The image sensor 12 is a CMOS sensor or a CCD sensor, and is configured to image an interior of the subject body in synchronization with the synchronization signal that is input from the connector 17 to generate the video signal relating to the subject body. The insertion section 11 is configured to emit illumination light from the distal end.

The insertion section 11 includes a portion configured to bend in response to operation of an operation knob at the operation unit 14, performed by an operator such as a doctor, and a portion configured to bend passively by external force, not via operation of the operation unit 14.

The operation unit 14 connects the insertion section 11 and the cable 15. The operation unit 14 includes, as operation knobs, an RL knob for bending the insertion section 11 rightward or leftward, and a UD knob for bending the insertion section 11 upward or downward. The operation unit 14 includes various switches.

A light guide is arranged inside the insertion section 11, the operation unit 14, and the cable 15. The light guide is connected to a light source apparatus 21 of the controller 20 via the connector 16 provided at the proximal end of the cable 15. Various signal lines are arranged inside the insertion section 11, the operation unit 14, and the cable 15. The signal lines are connected to an image processor 22 of the controller 20 via the connector 17 connected to the connector 16.

The light source apparatus 21 includes a light source such as a white LED, and emits illumination light. The illumination light emitted from the light source apparatus 21 is transmitted to the distal end of the insertion section 11 via the light guide and emitted from the distal end of the insertion section 11. The interior of the subject body is illuminated accordingly.

The image processor 22, as an external signal processor of the image sensor 12, processes the video signal obtained by the image sensor 12 of the insertion section 11. This processing includes the processing of conversion to a format whereby the video signal can be displayed on the monitor 30, e.g., gradation correction processing, etc. The image processor 22 generates a control signal for controlling the operation of the image sensor 12 and a reference clock (second clock) with a predetermined frequency, and inputs the generated control signal and second clock to the connector 17.

In FIG. 1, the image processor 22 and the light source apparatus 21 are arranged independently in the controller 20, but they may alternatively be configured as a single housing.

The monitor 30 is, for example, a liquid crystal monitor. The monitor 30 displays video and various kinds of information based on the video signal processed by the image processor 22, in synchronization with the second clock generated by the image processor 22.

Figure 2:
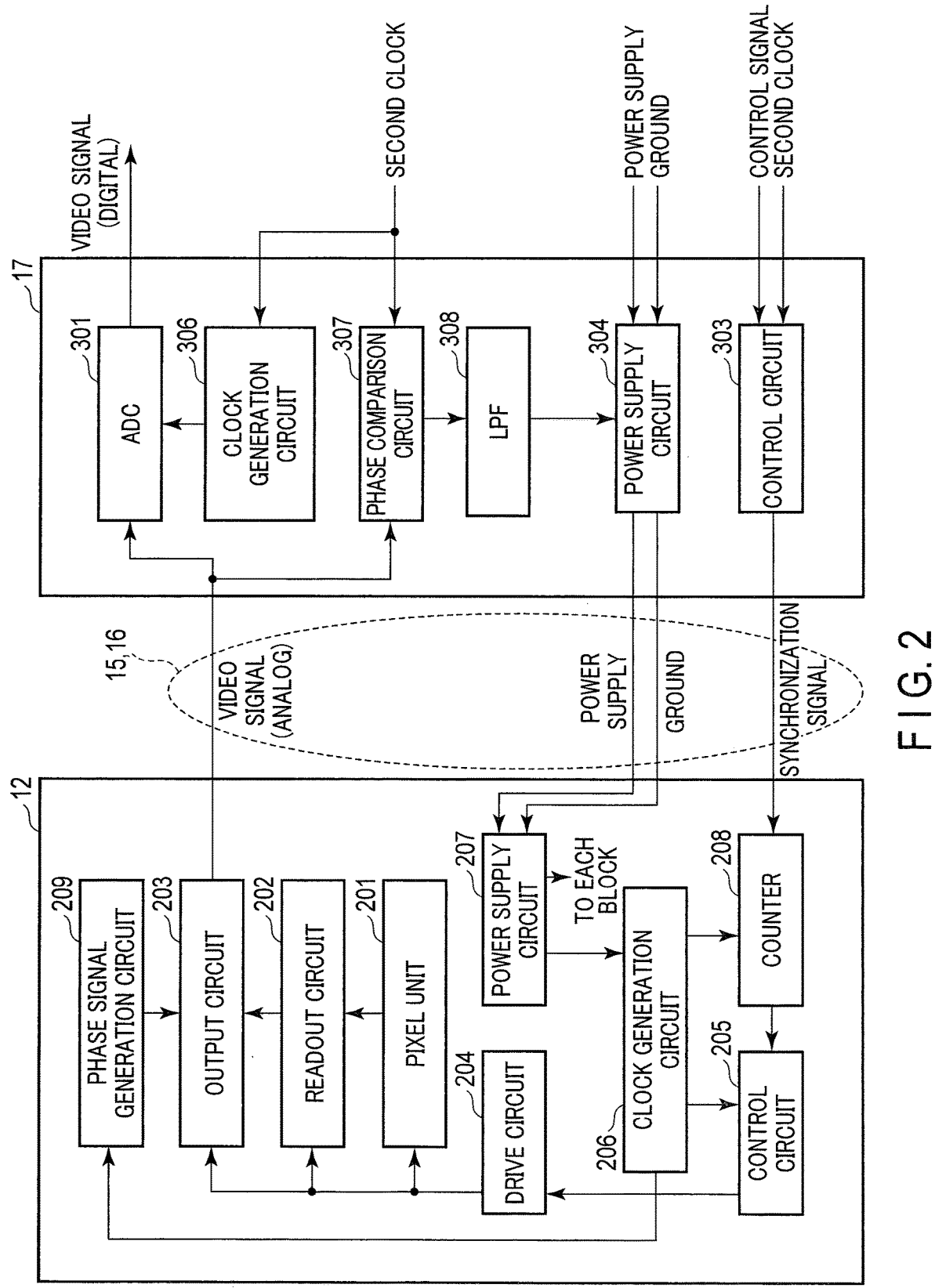
FIG. 2 is a diagram showing a detailed configuration of an image sensor and a connector according to the embodiment.

FIG. 2 shows the detailed configuration of the image sensor 12 and the connector 17 in the present embodiment.

As shown in FIG. 2, the image sensor 12 includes a pixel unit 201, a readout circuit 202, an output circuit 203, a drive circuit 204, a control circuit 205, a clock generation circuit 206, a power supply circuit 207, a counter 208, and a phase signal generation circuit 209. Each block of the image sensor 12 is constituted by, for example, hardware. However, some blocks such as the control circuit 205 and the like are not necessarily constituted by hardware, and may be constituted by software. Each block of the image sensor 12 may not be constituted by a single hardware or software unit, and may be constituted by a plurality of hardware or software units.

The pixel unit 201 includes a plurality of pixels arranged two-dimensionally. Each pixel is formed, for example, by a photodiode, and outputs an analog electronic signal (video signal) in accordance with incident light. The charge accumulation time (exposure time) of each pixel is controlled in accordance with a drive signal generated by the drive circuit 204.

The readout circuit 202 reads out a video signal from each pixel of the pixel unit 201 in accordance with the drive signal generated by the drive circuit 204, performs necessary analog processing, such as removal of reset noise and amplification processing on the read video signal, and then outputs the video signal to the output circuit 203. Here, the readout circuit 202 may be configured to read out a signal of the optical black region in the pixel unit 201 together.

According to the drive signal generated by the drive circuit 204, the output circuit 203 outputs, in different periods, to the connector 17 via the video signal line provided inside the cable 15 in an analog signal state, the video signal held in the readout circuit 202 and a phase signal that reflects a phase of a first clock input from the phase signal generation circuit 209.

The drive circuit 204 outputs drive signals to the pixel unit 201, the readout circuit 202 and the output circuit 203, based on the control signal from the control circuit 205.

The control circuit 205, as the first control circuit, counts the clock generated by the clock generation circuit 206 in response to the input of the synchronization signal (vertical synchronization signal and horizontal synchronization signal) input from the connector 17 via the cable 15, and outputs the control signal which indicates driving patterns of the pixel unit 201, the readout circuit 202, and the output circuit 203.

The clock generation circuit 206 includes a voltage control oscillation circuit (VCO), and generates a reference clock (first clock) of a predetermined frequency based on the power supply voltage input from the power supply circuit 207. The configuration of the clock generation circuit 206 is not particularly limited, as long as a clock of a predetermined frequency can be generated. However, since the clock generation circuit 206 is mounted on the image sensor 12, it is desirable that the clock generation circuit 206 be configured to be as small as possible, such as a configuration using a ring oscillator.

The power supply circuit 207 boosts or steps down the power supply voltage supplied from the connector 17 via the cable 15 as necessary, and supplies the voltage to each block of the image sensor 12. Furthermore, the power supply circuit 207 outputs the power supply voltage supplied from the connector 17 via the cable 15 to the clock generation circuit 206.

The counter 208 is connected to the control circuit 205 and the clock generation circuit 206. The counter 208 counts the first clock generated by the clock generation circuit 206 in response to the input of the synchronization signal from the connector 17, and when the count value of the first clock reaches the predetermined count value, the counter 208 notifies the control circuit 205 accordingly.

The phase signal generation circuit 209 is connected to the output circuit 203 and the clock generation circuit 206. The phase signal generation circuit 209 outputs, to the output circuit 203, a phase signal reflecting the phase of the first clock generated by the clock generation circuit 206.

The connector 17 includes an AD conversion circuit (ADC) 301, a control circuit 303, a power supply circuit 304, a clock generation circuit 306, a phase comparison circuit 307, and an LPF 308. Here, the function of each block of the connector 17 may be provided separately from the image sensor 12 inside the scope 10. For example, the function of each block of the connector 17 may be provided in, for example, the insertion section 11, the connector 16 or the operation unit 14 other than the connector 17.

The ADC 301 samples the video signal in synchronization with the AD drive clock generated by the clock generation circuit 306, and converts it into a digital signal.

The control circuit 303, as the second control circuit, receives input of the control signal from the image processor 22, counts the clock (second clock) input from the image processor 22, and generates a synchronization signal. Then, the control circuit 303 inputs the synchronization signal to the image sensor 12. As described above, the image sensor 12 operates by counting the clock generated by the clock generation circuit 206 in response to the synchronization signal.

The power supply circuit 304, for example, boosts or steps down the power supply voltage supplied from the image processor 22 as necessary, and supplies the voltage to each block of the connector 17. Furthermore, the power supply circuit 304 outputs, for example, the power supply voltage and the ground signal supplied from the image processor 22 to the image sensor 12, via the power supply line and the ground line provided inside the cable 15. The image sensor 12 operates based on these power supply voltages. Furthermore, the power supply circuit 304 outputs the power supply voltage reflecting the DC voltage input from the LPF 308 to the image sensor 12, via the power supply line provided inside the cable 15.

The second clock generated by the image processor 22 is input into the clock generation circuit 306. The clock generation circuit 306 generates an AD drive clock for operating the ADC 301 from the second clock.

The phase comparison circuit 307 is connected to the input terminal of the video signal of the connector 17, makes a phase comparison between the second clock and the phase signal reflecting the phase of the first clock transmitted from the output circuit 203 of the image sensor 12 together with the video signal, and outputs the phase difference signal indicating the phase difference between the first clock and the second clock.

The LPF 308 is a loop filter that integrates the phase difference signal input from the phase comparison circuit 307 and converts it into a DC voltage.

Hereinafter, a description will be given of the operations of the endoscope system 1 according to the present embodiment. First, the light source apparatus 21 and the image processor 22 of the endoscope system 1 are turned on. At this time, for example, the power supply voltage is supplied to the image sensor 12 of the scope 10 from the light source apparatus 21, and the image sensor 12 is powered on. In order to display the endoscope image, the control signal for starting the operation of the image sensor 12 and the second clock are input to the control circuit 303 of the connector 17 from the image processor 22.

The control circuit 303 generates synchronization signals (vertical synchronization signal and horizontal synchronization signal) in response to the inputs of the control signal and the second clock. The vertical synchronization signal is a synchronization signal indicating the start of one frame, which is the update period of the endoscope image on the monitor 30. The horizontal synchronization signal is a synchronization signal indicating the start of the output of one row (one line) in each frame. The control circuit 303 outputs the vertical synchronization signal, when it is time to output the vertical synchronization signal, while counting the second clock, and thereafter outputs the horizontal synchronization signal when it is time to output the horizontal synchronization signal.

The control circuit 205 of the image sensor 12 receives input of the signal of the synchronization signal count result from the counter 208, and generates a control signal for selecting the readout pixel row of the pixel unit 201 and for performing the pixel readout operation. That is, the control circuit 205 outputs the control signal to the drive circuit 204 so as to read out the video signal in the corresponding pixel row every time the control circuit 205 receives the horizontal synchronization signal.

The drive circuit 204 receives the control signal from the control circuit 205, and drives the readout circuit 202 to perform pixel driving so as to transfer the video signal from the pixels in the selected row of the pixel unit 201 to the readout circuit 202, and simultaneously to perform reset noise removal, etc. Furthermore, the drive circuit 204 drives the output circuit 203 so as to output, from the output circuit 203, the video signal read out to the readout circuit 202 and the phase signal reflecting the phase of the first clock from the phase signal generation circuit 209. That is, every time the horizontal synchronization signal is input to the control circuit 205 of the image sensor 12, the video signal for one row and the phase signal reflecting the phase of the first clock are output from the output circuit 203.

The video signal output from the output circuit 203 is converted into a digital signal in the ADC 301 of the connector 17 in synchronization with the AD drive clock generated in the clock generation circuit 306. This digital video signal is output to the image processor 22.

On the other hand, the phase signal reflecting the phase of the first clock output from the output circuit 203 is input to the phase comparison circuit 307. The phase comparison circuit 307 makes a phase comparison between the phase signal reflecting the phase of the first clock and the second clock, and outputs the phase difference signal indicating the phase difference between the first clock and the second clock. The LPF 308 integrates the phase difference signal, converts it into a DC voltage, and outputs it to the power supply circuit 304. The power supply circuit 304 receives output of the LPF 308, and controls the power supply voltage output to the power supply circuit 207 of the image sensor 12. The power supply circuit 207 outputs a power supply voltage corresponding to the power supply voltage input from the power supply circuit 304 to the clock generation circuit 206. The reference clock (first clock) of a predetermined frequency output from the clock generation circuit 206 is adjusted to have a frequency equal to that of the second clock.

The control circuit 205 operates so as to sequentially and repeatedly output a video signal for one row in accordance with the output of the counter 208, and outputs a video signal for one frame. After a certain accumulation time, the control circuit 205 receives the vertical synchronization signal from the control circuit 303 as the second control circuit, and starts the video signal output operation of the next frame.

As described above, it is desirable that the clock generation circuit 206 of the image sensor 12 be as small as possible. Here, there is a possibility that a comparatively large clock oscillator, such as a crystal oscillator, cannot be mounted on the image sensor 12 as the clock generation circuit 206. On the other hand, there is a high possibility that the ring oscillator can be mounted on the image sensor 12. However, the ring oscillator is dependent on the power supply voltage. Therefore, when a ring oscillator is used as the clock generation circuit 206, if the power supply voltage fluctuates due to the influence of temperature fluctuation or the like, there is a possibility that frequency fluctuation will occur in the first clock generated by the clock generation circuit 206. However, in the clock generation circuit 206, feedback control is performed so that the frequency of the first clock is equal to the frequency of the second clock, and thus the output of the video signal from the image sensor 12 and the display of the video by the image processor 22 can be synchronized.

As described above, according to the present embodiment, since the clock generation circuit is mounted inside the image sensor 12, it is unnecessary to transmit a clock to the image sensor 12. Therefore, it is not necessary to provide a signal line on the cable 15 for transmission of the clock, and it is possible to reduce the diameter of the cable 15 accordingly.

When the clock generation circuit is mounted on the image sensor 12, there is a possibility that the imaging operation of the image sensor 12 and the display operation of the image processor 22 cannot be synchronized. On the other hand, in the present embodiment, one PLL is formed between the image sensor 12 and the connector 17, and the first clock is generated so that its frequency is adjusted by the PLL to be equal to that of the second clock generated by the image processor 22. Thus, it is possible to generate the first clock synchronized with the second clock in the image sensor 12, and as a result, the imaging operation of the image sensor 12 and the display operation of the image processor 22 can be synchronized.

Hereinafter, modifications of the present embodiment will be described.

Modification 1

First, Modification 1 will be described. The above-described embodiment relates to a configuration example in which the video signal transmitted from the image sensor 12 to the connector 17 is an analog signal. On the other hand, Modification 1 is a configuration example in which the video signal transmitted from the image sensor 12 to the connector 17 is a digital signal.

FIG. 3 is a diagram showing the detailed configuration of the image sensor 12 and the connector 17 according to Modification 1. In FIG. 3, the same components as those in FIG. 2 are denoted by the same reference numerals as those in FIG. 2, and the description thereof will be omitted.

The connector 17 of Modification 1 includes an LVDS receiver 301a instead of the ADC 301 and the clock generation circuit 306. As will be described later, the LVDS receiver 301a separates the LVDS signal transmitted from the LVDS driver 203c of the image sensor 12 into a first clock and a video signal. Then, the LVDS receiver 301a outputs the video signal to the image processor 22, and outputs the clock to the phase comparison circuit 307.

In the image sensor 12 of Modification 1, the first clock generated by the clock generation circuit 206 is input to the frequency divider 210. The frequency divider 210 divides the input first clock at a predetermined frequency division ratio. For example, the frequency divider 210 sets the frequency of the first clock generated by the clock generation circuit 206 to $\frac{1}{10}$. The frequency division ratio of the frequency divider 210 can be appropriately set.

The counter 208 of Modification 1 counts the clock that is frequency-divided by the frequency divider 210 in response to the input of the synchronization signal, and when the count value of the clock has reached the predetermined count value, the counter 208 notifies the control circuit 205 accordingly.

The control circuit 205 of Modification 1 outputs the control signal to the pixel unit 201 and the readout circuit 202 in synchronization with the clock that is frequency-divided by the frequency divider 210. That is, in Modification 1, the pixel unit 201 and the readout circuit 202 are driven in synchronization with the frequency-divided clock.

The image sensor 12 of Modification 1 includes, instead of the output circuit 203, an ADC 203a, a transmission signal generation circuit 203b, and an LVDS driver 203c.

The first clock generated by the clock generation circuit 206 is input to the ADC 203a. The ADC 203a converts the video signal into a digital signal by sampling the video signal based on the first clock as an AD drive clock. That is, in Modification 1, the AD conversion is performed in synchronization with the first clock that is not frequency-divided.

The transmission signal generation circuit 203b generates a serial signal in which a phase signal reflecting the phase of the first clock generated by the clock generation circuit 206 is added to the digitized video signal, and outputs the serial signal to the LVDS driver 203c.

The LVDS driver 203c converts the serial signal generated by the transmission signal generation circuit 203b into a low voltage differential signal (LVDS signal), and outputs it to the connector 17 via a video signal line provided inside the cable 15.

As described above, in Modification 1, the video signal and the phase signal are transferred using the LVDS method, and this allows for the speedup of signal transfer as well as the reduction in the power consumption during signal transfer. In addition, as with the above-described embodiment, by constructing the PLL as a whole between the image sensor 12 and the connector 17, even if there is a frequency fluctuation, it is possible to generate the first clock synchronized with the second clock inside the image sensor 12.

Also, by frequency-dividing the first clock by the frequency divider 210, it is possible to generate the frequency of the clock for driving the pixel unit 201 and the frequency of the clock for driving the ADC 203a separately.

Modification 2

Next, Modification 2 will be described. Modification 2 is a modification to Modification 1, and is an example using a decoder 208a instead of the counter 208 as shown in FIG. 4. In Modification 2, the control circuit 303 receives the control signal from the image processor 22 as it is, not a synchronization signal. The decoder 208a decodes the control signal, and outputs the decoding result to the control circuit 205. The control circuit 205 receives the decoding result signal from the decoder 208a, and outputs the control signal indicating the driving patterns of the pixel unit 201 and the readout circuit 202.

In Modification 2 as described above, it is possible to generate the first clock synchronized with the second clock inside the image sensor 12 in the same manner as in Modification 1.

Modification 3

Figure 5:
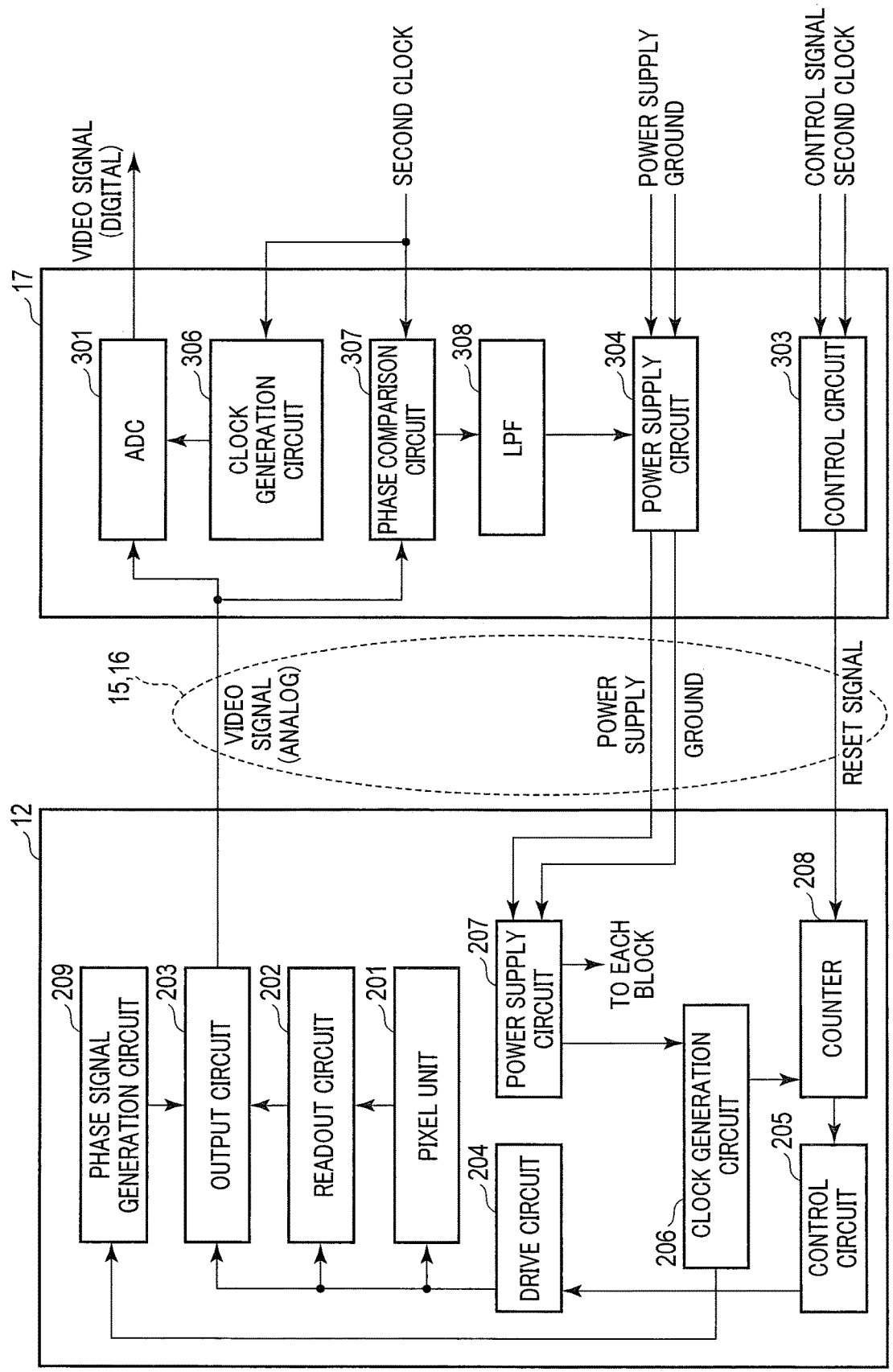
FIG. 5 is a diagram showing a detailed configuration of an image sensor and a connector according to Modification 3.

Next, Modification 3 will be described. FIG. 5 is a diagram showing the detailed configuration of the image sensor 12 and the connector 17 according to Modification 3. In FIG. 5, the same components as those in FIG. 2 are denoted by the same reference numerals as those in FIG. 2, and the description thereof will be omitted.

As shown in FIG. 5, in Modification 3, the control circuit 303 of the connector 17 generates a reset signal instead of the synchronization signal in response to the inputs of the control signal and the second clock. Then, the control circuit 303 inputs the reset signal to the counter 208 of the image sensor 12.

The counter 208 in Modification 3 also inputs the count value of the first clock to the control circuit 205. Here, the counter 208 in Modification 3 receives the reset signal from the control circuit 303, resets the count value of the first clock, and counts the first clock again.

The control circuit 205 in Modification 3 receives input of the count value of the first clock from the counter 208, and generates a control signal for selecting the readout pixel row of the pixel unit 201 and performing the pixel readout operation.

As described above, also in Modification 3, since a clock generation circuit is mounted in the image sensor 12, it is unnecessary to transmit a clock to the image sensor 12. Therefore, it is unnecessary to provide a signal line on the cable 15 for transmitting the clock, and it is possible to reduce the diameter of the cable 15 accordingly.

In addition, the reset signal for resetting the count value of the counter 208 serves to return the image sensor 12 to the initial state when an unexpected operation is performed. Thereby, the imaging operation of the image sensor 12 can be reset.

Here, FIG. 5 is a modification to FIG. 2, but a counter similar to that shown in FIG. 5 is applicable to the configuration of FIG. 3.

Modification 4

Figure 6:
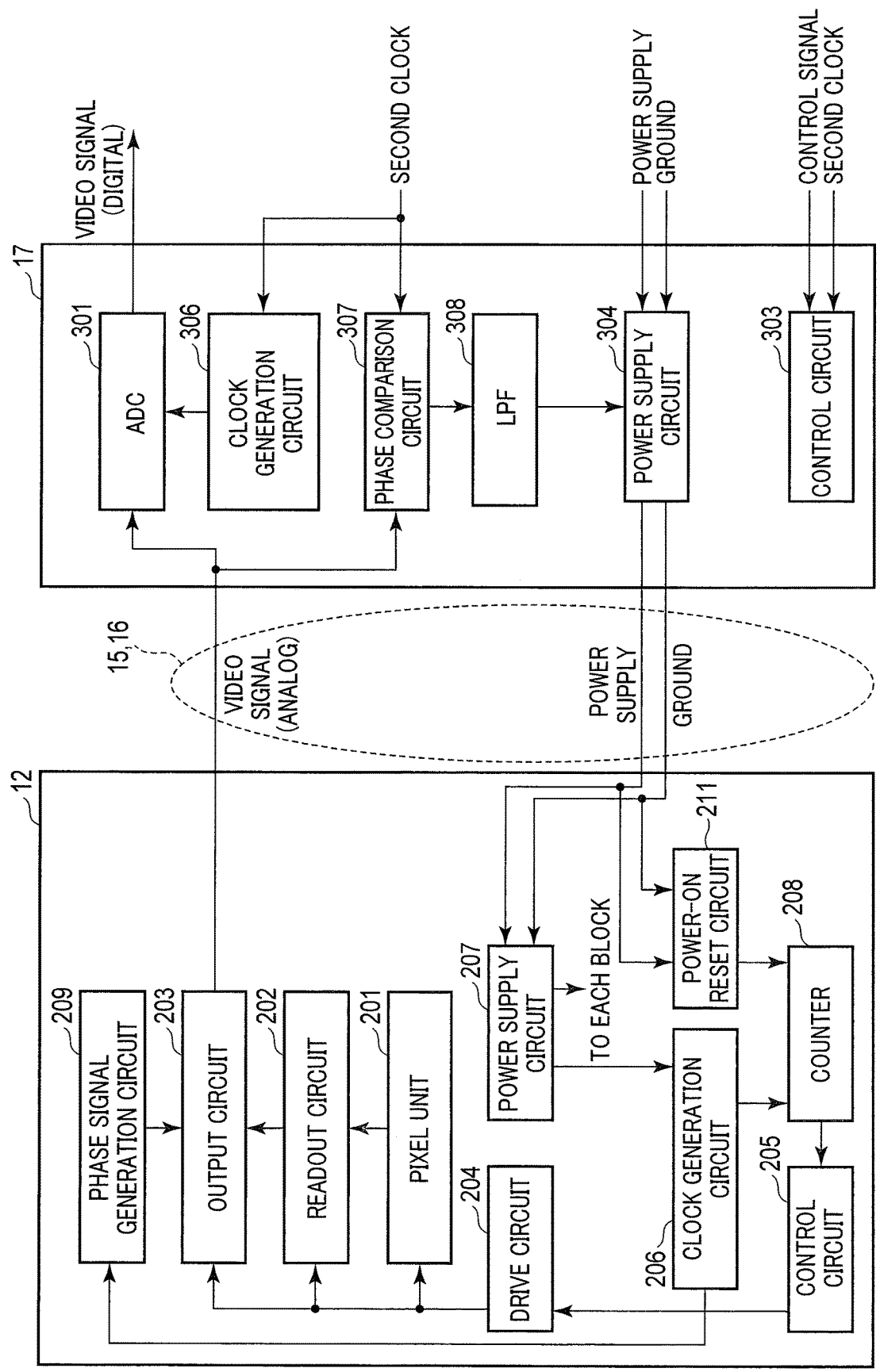
FIG. 6 is a diagram showing a detailed configuration of an image sensor and a connector according to Modification 4.

Next, Modification 4 will be described. FIG. 6 is a diagram showing a detailed configuration of the image sensor 12 and the connector 17 according to Modification 4. In FIG. 6, the same components as those in FIG. 2 are denoted by the same reference numerals as those in FIG. 2, and the description thereof will be omitted.

As shown in FIG. 6, in Modification 4, the image sensor 12 further includes a power-on reset circuit 211. The power-on reset circuit 211 is connected to the power supply line and the ground line between the power supply circuit 207 and the power supply circuit 304. Then, upon power-on of the endoscope system 1, the power-on reset circuit 211 inputs a reset signal to the counter 208. In addition to this, the power-on reset circuit 211 inputs a reset signal when unexpected power supply voltage fluctuation occurs, such as when the power supply voltage becomes lower than a predetermined voltage.

The counter 208 in Modification 4 also inputs the count value of the first clock to the control circuit 205. Here, the counter 208 in Modification 4 receives the reset signal from the power-on reset circuit 211, resets the count value of the first clock, and counts the first clock again.

The control circuit 205 in Modification 4 receives input of the count value of the first clock from the counter 208, and generates a control signal for selecting the readout pixel row of the pixel unit 201 and for reading out the pixel.

As described above, also in Modification 4, since a clock generation circuit is mounted inside the image sensor 12, it is unnecessary to transmit a clock to the image sensor 12. Therefore, it is unnecessary to provide a signal line on the cable 15 for transmitting the clock, and it is possible to reduce the diameter of the cable 15 accordingly.

In addition, the reset signal for resetting the count value of the counter 208 serves to return the image sensor 12 to the initial state when an unexpected operation is performed. Thereby, the imaging operation of the image sensor 12 can be reset by turning on the power supply again. Furthermore, in Modification 4, the reset signal is generated inside the image sensor 12.

Therefore, in Modification 4, it is unnecessary to provide a signal line for transmitting a reset signal, and the diameter of the cable 15 can be reduced accordingly.

Here, FIG. 6 is a modification to FIG. 2, but a counter similar to that shown in FIG. 6 is applicable to the configuration of FIG. 3.

Other Modifications

In the above embodiment and its modifications, an endoscope system has been exemplified. On the other hand, the imaging apparatus (scope 10) in the present embodiment does not necessarily need to be inserted into the body of the subject. For example, the imaging apparatus according to the present embodiment may be an extracorporeal camera that performs imaging from the outside of the body of the subject.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging apparatus arranged within an endoscope comprising an insertion section, the imaging apparatus comprising:

an image sensor arranged at a distal end of the insertion section; and a signal processor provided to a proximal end of the insertion section and electrically connected to the image sensor via a video signal line and a power supply line, wherein the image sensor comprises:
  a pixel configured to generate a video signal;
  a readout circuit configured to read out the video signal generated by the pixel;
  an output circuit configured to output the video signal read out by the readout circuit to the signal processor via the video signal line;
  a clock generation circuit configured to generate a first clock for driving the pixel, the readout circuit, and the output circuit; and
  a first control circuit configured to cause the output circuit to output the video signal and a phase signal of the first clock from the image sensor to the signal processor via the video signal line in accordance with the first clock and a synchronization signal generated by the signal processor, wherein the signal processor comprises a phase comparison circuit configured to make a phase comparison between the phase signal output from the output circuit and a second clock generated by the signal processor, and output a phase difference signal indicating a phase comparison result to the power supply line, and wherein the clock generation circuit is configured to generate the first clock based on a power supply voltage in accordance with the phase difference signal output to the power supply line.

2. An imaging apparatus arranged within an endoscope comprising an insertion section, the imaging apparatus comprising:
  an image sensor arranged at a distal end of the insertion section; and; and
  a signal processor provided to a proximal end of the insertion section and electrically connected to the image sensor via a video signal line and a power supply line, wherein the image sensor comprises:
  a pixel configured to generate a video signal;
  a readout circuit configured to read out the video signal generated by the pixel;
  an output circuit configured to output the video signal read out by the readout circuit to the signal processor via the video signal line;
  a clock generation circuit configured to generate a first clock for driving the pixel, the readout circuit, and the output circuit; and
  a first control circuit configured to cause the output circuit to output the video signal and a phase signal of the first clock from the image sensor to the signal processor via the video signal line in accordance with the first clock and a reset signal, wherein the signal processor comprises a phase comparison circuit configured to make a phase comparison between the phase signal output from the output circuit and a second clock generated by the signal processor, and output a phase difference signal indicating a phase comparison result to the power supply line, and wherein the clock generation circuit is configured to generate the first clock based on a power supply voltage in accordance with the phase difference signal output to the power supply line.

3. The imaging apparatus according to claim 2,
wherein the image sensor comprises a power-on reset circuit configured to output the reset signal to the first control circuit upon power-on.

4. An endoscope system comprising:
  an insertion section;
  an image sensor arranged at a distal end of the insertion section; and
  a signal processor provided to a proximal end of the insertion section and electrically connected to the image sensor via a video signal line and a power supply line, wherein the image sensor comprises:
  a pixel configured to generate a video signal;
  a readout circuit configured to read out the video signal generated by the pixel;
  an output circuit configured to output the video signal read out by the readout circuit to the signal processor via the video signal line;
  a clock generation circuit configured to generate a first clock for driving the pixel, the readout circuit, and the output circuit; and
  a first control circuit configured to cause the output circuit to output the video signal and a phase signal of the first clock from the image sensor to the signal processor via the video signal line in accordance with the first clock and a synchronization signal generated by the signal processor, wherein the signal processor comprises a phase comparison circuit configured to make a phase comparison between the phase signal output from the output circuit and a second clock generated by the signal processor, and output a phase difference signal indicating a phase comparison result to the power supply line, and wherein the clock generation circuit is configured to generate the first clock based on a power supply voltage in accordance with the phase difference signal output to the power supply line.

5. An endoscope system comprising:
  an insertion section;
  an image sensor arranged at a distal end of the insertion section; and
  a signal processor provided to a proximal end of the insertion section and electrically connected to the image sensor via a video signal line and a power supply line, wherein the image sensor comprises:
  a pixel configured to generate a video signal;
  a readout circuit configured to read out the video signal generated by the pixel;
  an output circuit configured to output the video signal read out by the readout circuit to the signal processor via the video signal line;
  a clock generation circuit configured to generate a first clock for driving the pixel, the readout circuit, and the output circuit; and
  a first control circuit configured to cause the output circuit to output the video signal and a phase signal of the first clock from the image sensor to the signal processor via the video signal line in accordance with the first clock and a reset signal, wherein the signal processor comprises a phase comparison circuit configured to make a phase comparison between the phase signal output from the output circuit and a second clock generated by the signal processor, and output a phase difference signal indicating a phase comparison result to the power supply line, and wherein the clock generation circuit is configured to generate the first clock based on a power supply voltage in accordance with the phase difference signal output to the power supply line.

6. The endoscope system according to claim 5, wherein the image sensor comprises a power-on reset circuit configured to output the reset signal to the first control circuit upon power-on.

* * * * *